United States Patent
Bos et al.

[11] Patent Number: 5,746,698
[45] Date of Patent: May 5, 1998

[54] METHOD AND DEVICE FOR DETERMINING BRACHIAL ARTERIAL PRESSURE WAVE ON THE BASIS OF NONIVASIVELY MEASURED FINGER BLOOD PRESSURE WAVE

[75] Inventors: Willem Jan Wubbo Bos, Bilthoven; Karel Hendrik Wesseling, HT The Hague, both of Netherlands

[73] Assignee: Nederlandse Organisatie voor Toegepast-Natuurwetenschappelijk Onderzoek TNO, Delft, Netherlands

[21] Appl. No.: 723,119

[22] Filed: Sep. 30, 1996

[30] Foreign Application Priority Data

Sep. 28, 1995 [NL] Netherlands ............... 1001309

[51] Int. Cl.$^6$ ................................ A61B 5/022
[52] U.S. Cl. ........................... 600/493; 600/485
[58] Field of Search ................ 128/672, 687, 128/691, 677, 680, 681, 678; 600/485, 500, 504, 490, 493, 491, 494

[56] References Cited

FOREIGN PATENT DOCUMENTS

| | | |
|---|---|---|
| 0 377 554 | 7/1990 | European Pat. Off. . |
| 2 279 752 | 1/1995 | United Kingdom . |
| WO 92/03966 | 3/1992 | WIPO . |
| WO 95/18564 | 7/1995 | WIPO . |

OTHER PUBLICATIONS

J. Virolainen, "Use of non-invasive finger blood pressure monitoring in the estimation of aortic pressure at rest and during the Mueller manoeuvre", *US National Library of Medicine*.

Primary Examiner—William E. Kamm
Assistant Examiner—Kennedy J. Schaetzle
Attorney, Agent, or Firm—Young & Thompson

[57] ABSTRACT

Method and device for determining a proximal arterial blood pressure waveform in a person, starting from a distally measured arterial pressure waveform, by first applying age-dependent waveform filtering to the distal pressure waveform, in order to obtain the proximal pressure waveform with mutually correct systolic, diastolic and mean pressure levels, and by then shifting the filtered pressure waveform by means of calibration to the correct proximal pressure level, for example by calibration of one level of the filtered systolic, diastolic or mean pressure levels with the corresponding proximal pressure level. This can be a single noninvasively measured systolic or diastolic or mean pressure level. The age for the purpose of the age-dependent waveform filtering is derived from the distally measured pressure waveform, for example by means of a trained neural network. The level shift in the filtered pressure waveform can be obtained by means of a regression equation which has entered in it only the filtered pressure waveform with corresponding systolic and diastolic pressure levels, or the above combined with a noninvasively measured single brachial pressure level.

10 Claims, 4 Drawing Sheets

METHOD AND DEVICE FOR DETERMINING BRACHIAL ARTERIAL PRESSURE WAVE ON THE BASIS OF NONIVASIVELY MEASURED FINGER BLOOD PRESSURE WAVE

In the human arterial system in which blood pressure is to be measured, pressure pulsations are produced into the aorta by the left ventricle of the heart. These pulsations propagate in the arterial system to the periphery and reach the latter in approx. 0.1 sec. These pulsations are sometimes recorded in the aorta, but are usually recorded at a peripheral point, by means of cannulas or catheters which are introduced into the body through the skin and are connected by way of tubing and stop valves to a manometer placed outside the body. Both the form of the pulsations and the DC level on which they are superimposed are important for experimental or clinical investigations and for monitoring patients. The parameters derived from the pressure pulse which are of importance for these medical purposes are the highest or systolic level, the lowest or diastolic level, and the true (integrated) mean or DC level of a heartbeat, as indicated in FIG. 1 in an example of a pressure wave as a function of time.

The arteries form a multiply branching system with a main stem and side branches, similar in many respects to a tree. At each branching point, and also over the length of an artery, the propagation properties of the system change as the result of the steadily decreasing diameter of the artery and compliance of the artery wall. Distortion of the pulse wave consequently occurs, in which case the amplitude and form thereof changes. When the pulse wave reaches the peripheral vascular beds with their relatively high resistance to flow, the main reflection of the pulse wave occurs, and the latter returns to the aorta and the heart. At this peripheral reflection point the main distortion of the pressure pulsation occurs and usually results in an amplification of the pressure pulsation.

Apart from the propagation of the pulse wave, associated with a pulse-type pressure and flow wave, there is also a steady (DC) flow of blood in the system from the heart to the periphery. This flow is driven by a pressure gradient which is usually negligible in the rather wide aorta and larger arteries, but is higher in the smaller arteries, for example in the extremities, and is highest in the acral parts of the circulation, such as in the hands, feet or ears. The result of the pressure gradient is that the pressure at peripheral points, such as at the ankle or wrist, is lower than centrally, in the aorta.

There are therefore two effects which distort the pressure pulsations in the arterial system: 1) the propagation of the pressure wave, and 2) the gradient of the pressure. Both are largest in the peripheral parts of the arterial system. As an illustration, an example is given in FIG. 2 of the simultaneous measurement relative to time of the blood pressure in the aorta (curve a), which is measured just behind the aortic valve, and the blood pressure (curve b) in the middle finger of the left hand of the same person, recorded in a catheterization chamber.

Ideally, blood pressure should therefore be measured centrally in the aorta. In practice, this is seldom done because the aorta lies deep in the human body and can be reached from the outside only by means of a long tubing which is inserted from a peripheral point where the arteries lie closer to the skin. In many branches of medicine one therefore has to be satisfied with peripheral pressure waveforms and levels. This has led to standardization at fixed peripheral points, in order to accumulate as much experience as possible and be able to recognize anomalies in the measurements. In anaesthesiology, for example, arterial pressure is virtually exclusively measured using a small cannula inserted percutaneously into the radial artery at the wrist, the small cannula reducing any risk for the patient. Other medical specialists give preference to cannulation of the brachial artery at the elbow, because this point is situated less peripherally and lies closer to the point where systolic (maximum), diastolic (minimum) and mean pressure levels of the pulsations are also measured with a cuff. This facilitates the comparison of invasively and noninvasively measured pressures at this point.

More recently, it has become possible to measure pulsations noninvasively at peripheral points, i.e. without puncturing the skin and inserting a cannula. For instance, pressure measuring devices, such as, for example, the Finapres sphygmomanometer, which continuously and reliably measure calibrated arterial finger pressures in humans using a volume clamping technique are known. Devices have also been developed for measuring pulsations in the wrist and the upper arm. Such measurements are, of course, also subject to the adverse influence of the effects of pressure propagation and pressure gradient encountered in invasive measurements. The abovementioned Finapres device is widely used by medical specialists who are interested in and have experience with proximal, for example brachial, arterial pressures in the upper arm. Differences have been found here between the intrabrachial and finger pressures, and a number of publications have described relative offsets and scatter in pressure levels and distortion in pulse waveform, with the result that the contribution of these measurements to diagnostics is limited.

In order to increase this applicability of finger pressure measurements, an obvious and, on the face of it, satisfactory solution would be the calibration of finger pressure levels on the basis of the results of one or more noninvasively measured systolic and diastolic levels of the upper arm. This could easily be carried out by means of a microprocessor for correcting each sample taken in the finger pressure waveform. Finger pressure calibrated in this way could then be used to monitor and record any heartbeat-to-heartbeat change in blood pressure. This approach is known, but has a number of disadvantages:

1) Although the upper (systolic) and lower (diastolic) pressure levels of the finger pressure waveform have been corrected in this way, the waveform itself is only stretched or shrunk and shifted in level here, but not changed. Any distortion of pulse form existing between intrabrachial pressure and finger pressure remains uncorrected. In particular, this is the case as regards the mean pressure levels. The mean pressure level of a brachial pulse pressure is typically up one third of the pressure of the diastolic level. However, for finger pressure pulsations it is a quarter of the pressure of the diastolic level. Since after correction the pulse pressures have been made identical, but the waveform has not been affected, the mean pressure of the finger pulsation is underestimated by approximately one twelfth of the pulse pressure or up to 20 mmHg in individual cases.

2) The usual non-invasive technique for establishing the systolic and diastolic pressure levels in the brachial artery is the so-called Riva-Rocci/Korotkoff (RRK) technique. This technique has the tendency to underestimate systolic pressure levels and to overestimate diastolic pressure levels. The result of this is that intrabrachial pulse pressures are underestimated by the non-invasive technique. Consequently, in the case of finger pressure pulsations which are corrected by levels obtained by the RRK technique, the brachial pressures are also underestimated.

3) The RRK technique cannot easily be mechanized. The Korotkoff sounds which are generated under the cuff and which are heard by the clinician are weak and are easily disturbed by ambient noises. They may also fool clinicians and computer programs alike, through the fact that auscultatory dead gaps occur, in which no sounds are heard, but diastolic pressure has not yet been reached. Furthermore, depending on circumstances not known to a computer program, such as the panting of a patient exerting himself physically, special measures have to be taken in the detection and interpretation of sounds and levels.

The object of the invention is to overcome the above problems and in general, on the basis of a distally determined pressure waveform, to obtain a proximally correct pressure waveform, in which the waveform, the pressure pulse amplitude and the relative levels of systolic, diastolic and mean pressure are all quantitatively correct and are also positioned at the correct proximal level.

This is achieved according to a first aspect of the invention by a method for determining a proximal arterial pressure waveform in a person, starting from a distally measured arterial pressure waveform, by first applying age-dependent waveform filtering to the distal pressure waveform, in order to obtain the proximal pressure waveform with mutually correct systolic, diastolic and mean pressure levels, and by then shifting the filtered pressure waveform by means of calibration to the correct proximal pressure level.

According to a second aspect of the invention, this is achieved by a device for carrying out the abovementioned method, wherein the device is provided with a finger sphygmomanometer with measuring head and finger pressure cuff, an upper arm pressure cuff with electromanometer, and a control and processing unit, which unit comprises at least an inverse age-dependent filter for filtering the arterial finger pressure waveform, and a calibration circuit for shifting the filtered pressure waveform to the brachial pressure level.

The invention will be explained in greater detail on the basis of an embodiment with reference to the drawings, in which.

Figure 1:
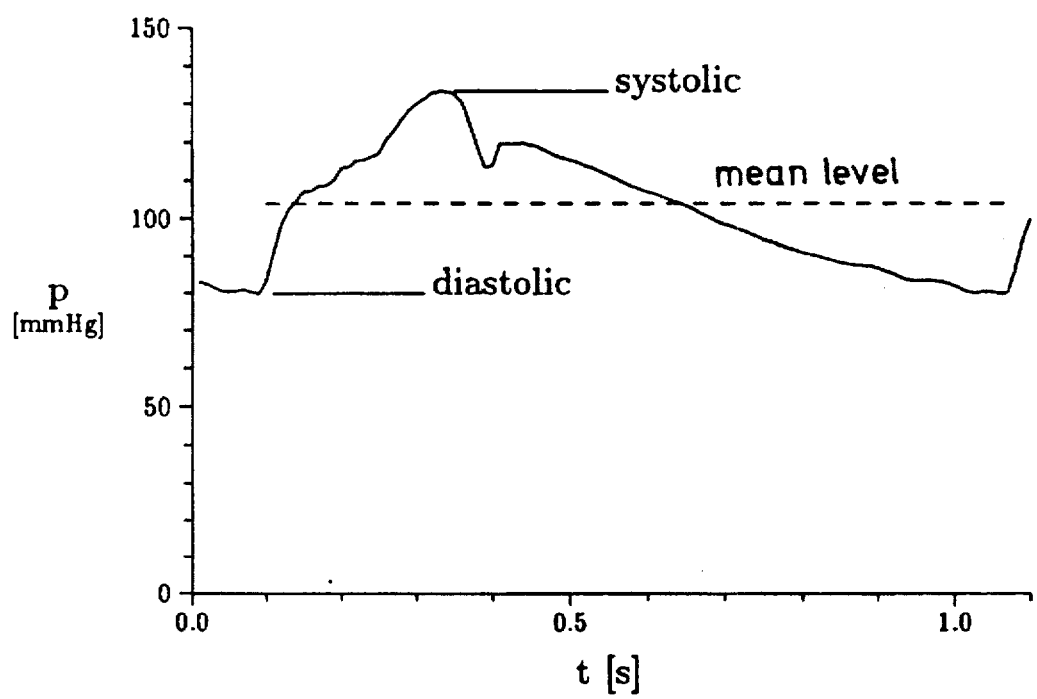
FIG. 1 shows an example of a blood pressure wave as a function of time.
Figure 2:
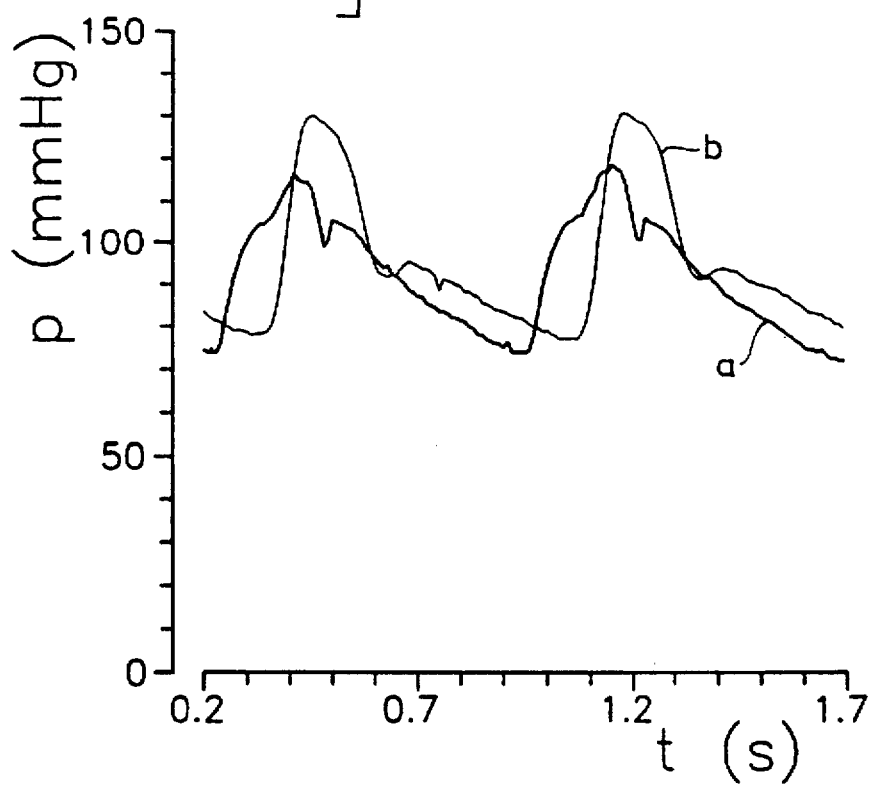
FIG. 2 shows an example of a blood pressure wave in the aorta and in a finger of the same person.
Figure 3:
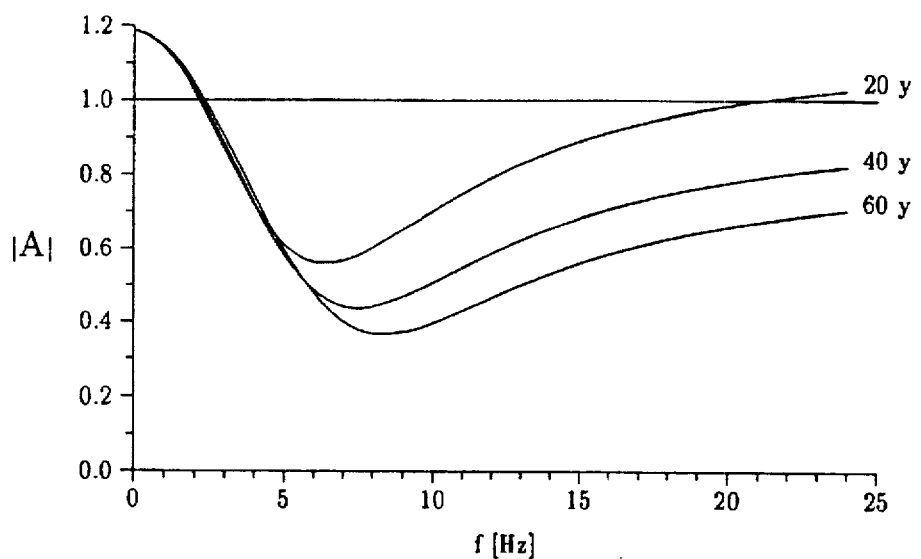
FIG. 3 shows an example according to the invention of the required filter response for persons of different ages.

It is known per se, from the article "Reconstruction of brachial arterial pulsation from finger arterial pressure" in Proc. 12th Int. Conf. IEEE Eng Med Biol Soc 1990; 12:1046–1047 (Gizdulich P., Wesseling K. H.), to use a filter in order to filter the pulsations obtained at the finger to approximate an intrabrachial waveform. However, these filters were found to be too inaccurate for the abovementioned approximation, in particular in older persons. It has now, surprisingly, been found that age-dependent filtering is in fact satisfactory. For instance, FIG. 3 gives an example of the required filter response for persons of three different ages (20, 40 and 60 years). For this compensation, the age of the person or patient must be entered into the filtering device, in order to obtain the filtering effect correctly for each person. This requires an additional action, but this action can be avoided by connecting the filter to an artificial neural network. The fact is that it has unexpectedly been found that the age of a person can be derived reliably from the pressure pulsation measured in the finger with a finger sphygmomanometer by using a well-trained neural network.

Figure 4:
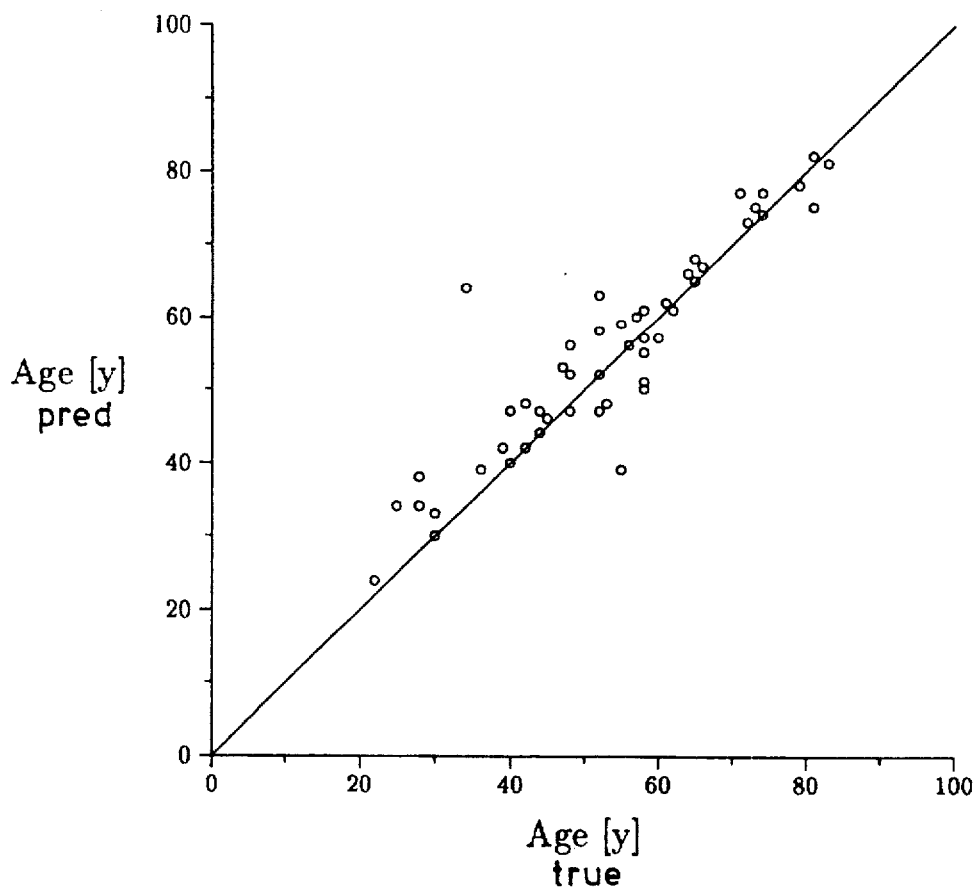
FIG. 4 shows an example according to the invention of an estimate of the age derived from the waveform of the pressure pulsation.

From the waveform of the arterial pressure pulsation, for example measured in the finger, an estimate of the age of the person can be given. FIG. 4 gives an illustration of the effectiveness of this approach. If the age is derived from this estimate, this can be entered as a parameter into the filtering device.

Once the correct pulse waveform and amplitude have been obtained in the inverse filtered waveform, calibration of one pressure level from the various possible pressure levels, namely systolic level, diastolic level and mean level, is sufficient. Theoretically, the best calibration is obtained from the highest, i.e. systolic, pressure. This calibration, based on systolic pressure, can be carried out in a suitable manner by using the return-to-flow method. This method is in itself not used much, since it provides only one of the two main arterial pressure levels, but in this case this method is very advantageous. In this case an upper arm cuff is rapidly inflated to a suprasystolic level. During the subsequent slow deflation the cuff pressure is read at the moment when the first pulsation occurs distally from the cuff, for example as detected in an ultrasound arterial flow velocity wave distally from the deflating cuff, as detected by an observer using a stethoscope, by palpation of the radial artery in the wrist, by observation of a change in colour of the blanched skin, or by plethysmography.

A particularly advantageous solution is obtained when the upper arm cuff is placed proximally from a finger pressure sphygmomanometer on the same arm. In that case the finger pressure sphygmomanometer can be used to detect the first pulsation which passes under the cuff on deflation. Since the sphygmomanometer already contains a source of compressed air, the inflation and deflation of the cuff can be carried out largely by means of available components. An addition to the microprocessor program inside the sphygmomanometer then allows the detection of the moment of return-to-flow and the reading of the corresponding systolic upper arm pressure.

An even more accurate solution can be obtained if the systolic pressure level associated with the return-to-flow is not used directly to shift the waveform, but is entered in a regression equation, the coefficients of which are obtained from a learn population of persons. For this purpose, in an example, the blood pressure of 53 persons varying in age from 22 to 83 years was measured invasively in the brachial artery, was measured in the finger of the contralateral arm with a sphygmomanometer, and systolic pressures were measured with a cuff on the upper arm proximally from the finger sphygmomanometer by means of return-to-flow. A regression equation was established from this as follows:

$$p_c^f(t) = p^f(t) + 18.7 + 0.44\, p_s^{rf} - 0.34 p_d^f - 0.36 p_s^f \tag{1}$$

in which $p_c^f(t)$ is the filtered, corrected finger pressure waveform as a function of time, $p^f(t)$ is the age-dependent inverse filtered waveform, $p_s^{rf}$ is the return-to-flow systolic pressure, $p_d^f$ is the filtered diastolic pressure and $p_s^f$ is the filtered systolic pressure.

In the event of a return-to-flow systolic level not being available, a suitable, but somewhat less perfect correction can be obtained in a similar way by using only pressure levels measured on the finger pressure pulsation according to $$p_c^f(t) = p^f(t) + 13.6 - 0.57\, p_d^f + 0.19 p_s^f \qquad (2)$$

with the same meanings for the symbols as in the previous equation.

It is remarkable that the finger pressure pulsation according to the invention can be used to establish the age of the person, following which the coefficients of the age-dependent filter are then determined. This filter ultimately provides a brachial artery-like pulsation, the DC level of which can be corrected using pressure levels of the filtered finger pressure. The fact that this is possible is a result of an apparent physiological property that low pulse pressures at a high DC pressure need a downward correction, while high pulse pressures at a low DC pressure must be corrected upwards.

Another solution is a correction of the mean pressure level by using an oscillometric mean pressure of an upper arm cuff, which is a known and fully automated technique of acceptable reliability.

Yet another solution is to obtain a diastolic level correction by an RRK, or an oscillometric diastolic level. Since this is the most difficult level, which can be obtained noninvasively, the use of this solution is in fact possible, but less advantageous.

The abovementioned method is not limited to the correction of finger pressure to intrabrachial pressure, but can also be used for the correction of any distally measured pressure to any more proximally or centrally present pressure, and vice versa.

Figure 5:
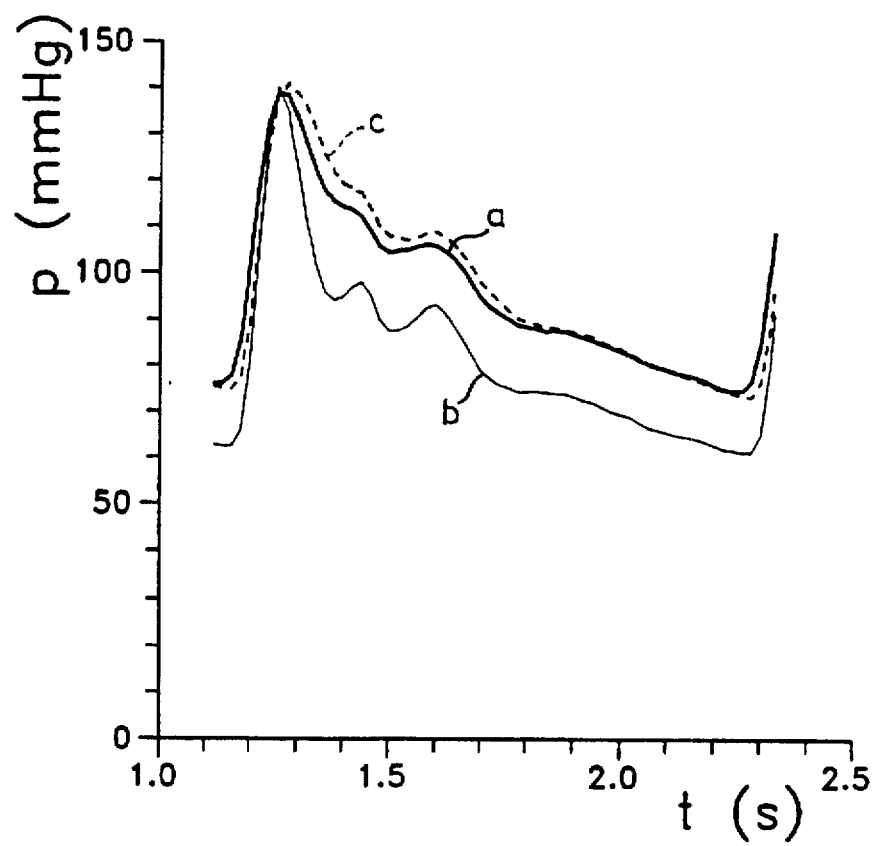
FIG. 5 shows an example according to the invention of a comparison between an original intrabrachial pressure pulsation, an original noninvasively measured arterial finger pressure pulsation and a pressure pulsation corrected from the latter.

FIG. 5 gives an example of the effect of the invention on an individual pressure wave. Three pulses are indicated, namely the original intrabrachial pressure pulsation as curve a (thick line), the original noninvasively measured arterial finger pressure pulsation as curve b (fine line), and the corrected pressure pulsation as curve c (dashed line). The reconstructed intrabrachial pulsation c is delayed somewhat in time relative to the original intrabrachial pulsation a, as a result of the travel time in the arteries of the arm to the finger, and as a result of filter delay. The steepness of the systolic upstroke and the general form are nearly identical to the original. The same applies to the pressure levels, although the levels are not always found as close together in different persons as indicated here.

Using the abovementioned method, which is carried out with the device to be described below, a proximal or, for example, brachial blood pressure which is correct both in form and level is therefore determined from a non-invasive recording of the distal or finger blood pressure. In other words, the proximal blood pressure determined by way of a correction from this distal or finger blood pressure comes sufficiently close to the pressure measured intraarterially in the brachial artery to fall well within the standards of the Association for the Advancement of Medical Instrumentation.

Figure 6:
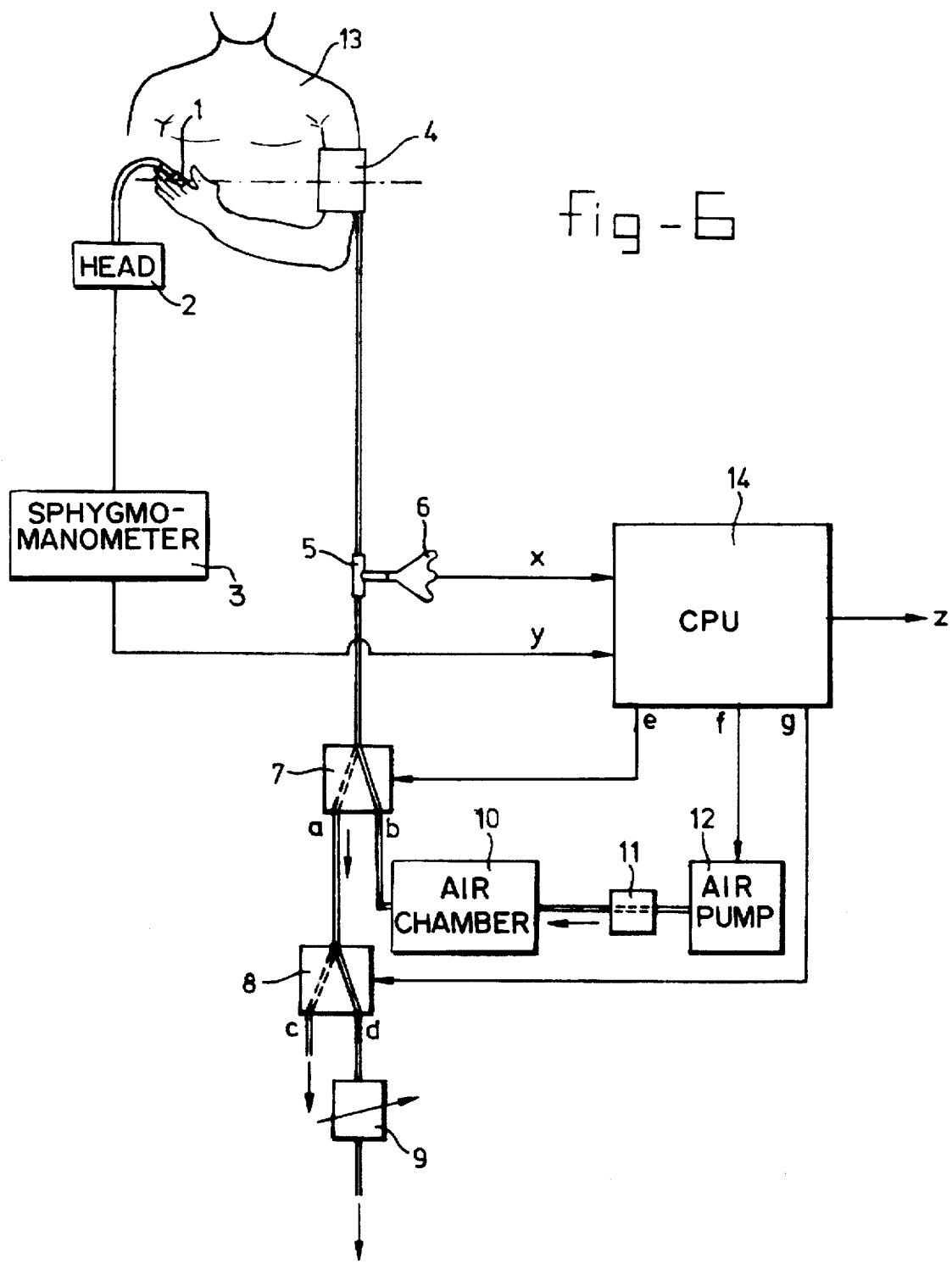
FIG. 6 shows a diagram of a device according to the invention.

The device according to the invention is shown diagrammatically in FIG. 6. It consists of a known standard finger sphygmomanometer, for example the commercially available Ohmeda 2300 Finapres. The cuff 1 of the sphygmomanometer is wound around a finger of the person 13 to be examined and is connected to the measuring head 2 of the sphygmomanometer 3. An ordinary upper arm pressure cuff 4 is wound around the same arm as that on which the finger cuff 1 has been placed. The center of the finger cuff 1 and the center of the upper arm cuff 4 are at the same hydrostatic level. The upper arm cuff 4 is connected by way of a tubing to a T-piece 5. The through channel of the T-piece 5 is connected to an electrically controllable changeover switch 7. The side branch of the T-piece 5 is connected to an electromanometer 6. The outlet a of changeover switch 7 is connected to a second electrically controllable changeover switch 8. The outlet c of changeover switch 8 is vented without restriction to the outside air, and the outlet d of changeover switch 8 is also vented to the outside air by way of a valve which requires setting only once. The outlet b of changeover switch 7 is connected to an air chamber 10, which is fed from an air pump 12 by way of a pressure relief valve 11 which requires setting only once. Changeover switch 7 is set by way of a signal e, changeover switch 8 is set by way of a signal g, and the pump is switched on and off by way of a signal f. The signals e, f and g are supplied by a control and processing unit 14, for example a personal computer provided with a real-time interface (RTI) card. The measurement signal x from the electromanometer 6 and the measurement signal y from the sphygmomanometer 3 are fed to an analog-digital converter accommodated in the RTI card. Said RTI generates an output signal z by way of a digital-analog converter. Said output signal presents the distal or brachial blood pressure curve corrected as regards form and level.

A program which constantly monitors the signals x and y and generates the signal z from them is run in the computer. In the finger blood pressure signal y, the heartbeats are detected, and the upper pressure (systolic), the lower pressure (diastolic) and the mean pressure are measured and determined. In normal operation the sphygmomanometer 3 measures the finger blood pressure and generates the signal y. This signal is sampled, filtered and shifted in level, following which the output signal z is produced.

The mode of operation is as follows. The changeover switch 7 is in position a, and changeover switch 8 is in position c. The cuff 4 is consequently in communication with the outside air and is at zero pressure. Any desired pressure, which can be equal to zero, prevails in the air chamber 10. At a certain moment determined by the computer or a user, the air pump 12 is switched on by way of the signal f. The air pump forces a quantity of air into the air chamber 10 by way of the valve 11 for a regular period. Changeover switch 7 is then placed in position b, and cuff 4 is quickly filled up to a pressure which is approximately 50 mmHg above the upper pressure (systolic) measured in the finger. The cuff pressure is measured by means of manometer 6 and fed to the computer by way of a signal x. Changeover switch 8 is now placed in position d, and immediately afterwards changeover switch 7 is placed in position a, and the air pump 12 is switched off. The pressure in cuff 4 now equalizes gradually with the outside air by way of the tubing, the T-piece 5, the changeover switches 7-a and 8-d and the valve 9.

Due to the fact that cuff 4 was inflated initially to a suprasystolic pressure, the blood supply to the finger has stopped, and no further pulsations are recorded by the sphygmomanometer 3 and detected by the computer in the signal y. After some time, the pressure in the cuff has now dropped so far that it is below the level of the systolic upper pressure. At that moment, initially small pulsations come through again and are recognized by the computer in signal y. This continues until, for example, three to five pulsations have been recognized in uniform rhythm. The first pulsation gives the moment of return-to-flow, and the corresponding pressure x, stored in the memory, in cuff 4 is the systolic or upper pressure in the upper arm. This pressure is then used to apply or renew the level correction described earlier in the formula in equation (1). So long as such a return-to-flow determination is not available, the level correction is carried out by way of the formula in equation (2).

The age-dependent filter which from the finger pressure constructs a blood pressure curve which is virtually identical in shape to the blood pressure curve in the upper arm has the characteristics shown in FIG. 3. The filter action is obtained by a cascade connection of three filters. The first filter is a high-emphasis filter, which shows a dip at the frequency where the initially flat characteristic passes into a second-order rising characteristic. Frequency and depth of the dip depend on age. The first filter is followed by a second and an identical third filter. They are first-order low-pass filters with a cut-off frequency which again depends on age.

The following is a computer program which simulates the desired filter:

```
VAR i: ARRAY [0..2] OF REAL;
a0,a1,a2,a3,a4,a5. (* filter coefficients *)
A,a,B,b. (* help variables *)
freq: REAL; (* filter frequency *)
PROCEDURE initialize(age:REAL);
BEGIN
  A:=0.0; a:=0.0; B:=0.0; b:=0.0;
  i[0]:=0.0; i[1]:=0.0; i[2]:=0.0;
  freq:= -25.52 + 4.537 * ln(age);
  a0 := 0.8426;
  a1 := 0.6889 - 0.0006 * age;
  a2 := a1;
  a3 := -0.5947 * (freq - 1.0);
  a4 := freq;
  a5 := 1.0 - a3 - a4
END initialize;
PROCEDURE agefilter(x:REAL):REAL;
VAR f: REAL;
BEGIN
  i[2]:=i[1]; i[1]:=i[0]; i[0]:=x;
  f:= (a3*i[0] + a4*i[1] + a5*i[2]) / a0 (* first filter *)
  A:=A-a+f; a:=a1*A; (* second filter *)
  B:=B-b+a; b:=a2*B; (* third filter *)
  RETURN b
END agefilter;
```

This age filter algorithm can be set up on the basis of the responses from FIG. 3, the logarithmic relation between frequency and age being derived in a special way.

Figure 7:
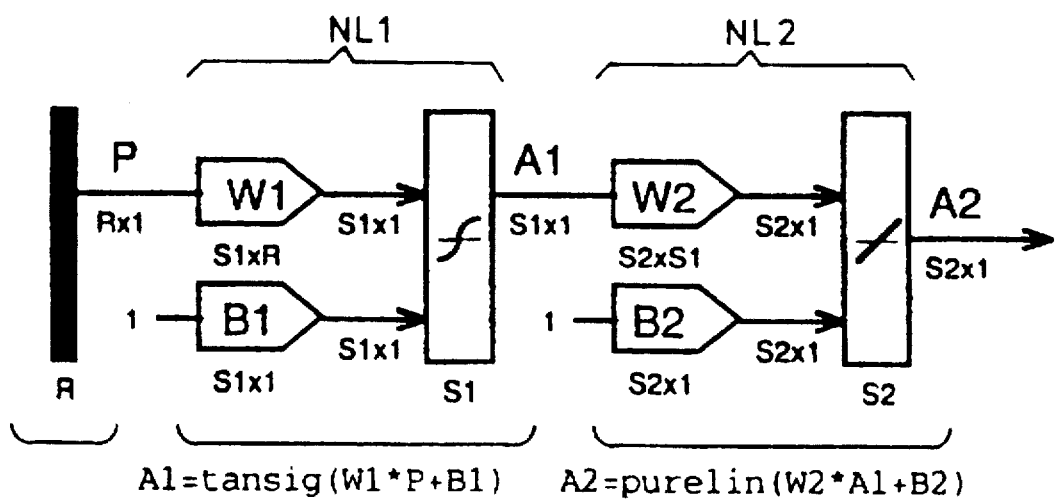
FIG. 7 shows an example of a neural network used in the device of FIG. 6.

However, it is possible according to the invention to use a neural network for the age-dependent filter, as indicated as an example in FIG. 7. This network consists, for example, of an input layer R, a first neuron layer NL1, and a second neuron layer NL2. A curve is fed into the input layer, and the network calculates the age by way of a non-linear filter (neuron). In this way, the network obtains at the input R the values of the derivative of the pressure curve at intervals of 20 ms in time. There are twenty-two of these inputs in the input layer. The first input acquires the value of the derivative at the beginning of the heartbeat, the second input acquires that of 20 ms later, and so on, until the first twenty inputs have acquired a value. Input 21 receives the value of the mean blood pressure and input 22 receives the value of the heart frequency. These input values propagate by way of known weighting factors W1, which are found by allowing the network to learn on known waveforms and ages, to an intermediate layer S1 of non-linear nodes. By way of a second set of weighting factors W2, which have been obtained in the same way as the presettings B1 and B2, the output signals Al propagate from the intermediate nodes to the output S2. From this output, a one-dimensional output signal A2 is obtained, by means of which the estimated age is given in years.

In order to indicate the full extent of effectiveness of the method and device according to the invention on pressure levels, results obtained in persons aged from 20 to 80 years are given below. Some of them were young, healthy volunteers, and others were patients suspected of having (cuff) hypertension, while others were healthy older persons. The mean intrabrachial pressure levels and standard deviation of the group are specified in the table below under "brachial". Further pairs in the columns specify the mean differences and standard deviation of the finger blood pressure relative to the intrabrachial pressure (fin-bra) for age-dependent filtered finger pressure (filt-bra), for filtered finger pressure shifted according to the second equation without return-to-flow (shifted), and finally for filtered finger pressure after return-to-flow correction according to the first equation (corrected).

| level | brachial | | fin-bra | | filt-bra | | shifted | | corrected | |
|---|---|---|---|---|---|---|---|---|---|---|
| | m | s | m | s | m | s | m | s | m | s |
| s | 169 | 33 | -5.4 | 15 | 8.1 | 1.1 | -0.0 | 13 | 3.7 | 7 |
| d | 89 | 17 | -8.5 | 11 | 8.2 | 12 | 0.0 | 8 | 1.0 | 5 |
| m | 118 | 22 | -13.2 | 11 | 7.0 | 12 | -1.1 | 9 | 0.7 | 5 |
| p | 80 | 23 | 3.1 | 12 | -0.0 | 9 | -0.0 | 9 | | |

The pressures and differences are indicated as mean and standard deviation. Four results are given, namely for systolic pressure (s), for diastolic pressure (d), for mean pressure (m), and for pulse pressure (p). The pulse pressure is not an independent measurement because it gives the difference between systolic and diastolic pressure. The return-to-flow corrected results are obtained from a subgroup of 29 mostly older persons for whom a return-to-flow measurement was available. The mean difference and standard deviation lie within the AAMI limits (±5±8 mmHg) and are small enough, so that a continuous brachial pressure signal for monitoring and partial diagnostic purposes is obtained.

We claim:

1. Method for determining a proximal arterial blood pressure waveform in a person, starting from a distally measured arterial pressure waveform, comprising the steps of: applying age-dependent waveform filtering to the distal pressure waveform, in order to obtain the proximal pressure waveform with mutually correct systolic, diastolic and mean pressure levels, and calibrating the filtered pressure waveform to the correct proximal pressure level.

2. Method according to claim 1, further comprising the step of calibrating one level of the filtered systolic, diastolic or mean pressure levels with the corresponding proximal pressure level.

3. Method according to claim 2, wherein the step of applying age-dependent waveform filtering converts a pressure waveform measured noninvasively on the finger into an intrabrachial pressure waveform, and wherein the step of calibrating the filtered pressure waveform calibrates the corresponding pressure level by means of a single, noninvasively measured, systolic or diastolic or mean brachial pressure level.

4. Method according to claim 3, wherein the abovementioned corresponding brachial pressure level is the systolic pressure level, and further comprising the steps of measuring the systolic pressure level with a pressure cuff on the upper arm, and of measuring the arterial finger pressure with a pressure cuff on a finger on the same arm for determining a moment of return-to-flow of the blood.

5. Method according to claim 3, wherein the level of shift of the filtered pressure waveform is obtained by means of a regression equation, which has entered in it not only the filtered pressure waveform with corresponding systolic and diastolic pressure levels, but also a noninvasively measured single brachial pressure level.

6. Method according to claim 1, further comprising the step of deriving an age for the age-dependent waveform filtering from the distally measured pressure waveform.

7. Method according to claim 6, wherein the step of deriving the age comprises the step of using a trained neural network.

8. Method according to claim 1, further comprising the step of measuring the abovementioned pressure waveform and pressure levels noninvasively.

9. Method according to claim 1, wherein the level of shift of the filtered pressure waveform is obtained by means of a regression equation, which has entered in it only the filtered pressure waveform with corresponding systolic and diastolic pressure levels.

10. Device for carrying out the method according to claim 1, which device is provided with a finger sphygmomanometer with measuring head and finger pressure cuff, an upper arm pressure cuff with electromanometer, and a control and processing unit, which unit comprises at least an inverse age-dependent filter for filtering the arterial finger pressure waveform, and a calibration circuit for shifting the filtered pressure waveform to the brachial pressure level.

* * * * *

UNITED STATES PATENT AND TRADEMARK OFFICE
CERTIFICATE OF CORRECTION

PATENT NO. : 5,746,698
DATED : May 5, 1998
INVENTOR(S) : Willem Jan Wubbo BOS et al.

It is certified that error appears in the above-indentified patent and that said Letters Patent is hereby corrected as shown below:

On the title page, item [54] and col. 1, line 4

In the title, change "NONIVASIVELY" to --NONINVASIVELY--.

Signed and Sealed this

Fifth Day of October, 1999

Attest:

Q. TODD DICKINSON

Attesting Officer

Acting Commissioner of Patents and Trademarks